United States Patent [19]

Schneider et al.

[11] Patent Number: 4,550,106
[45] Date of Patent: Oct. 29, 1985

[54] 4-PHENYL-4,5,6,7-TETRAHYDRO-THIENO[2,3-C]PYRIDINES AND SALTS THEREOF, COMPOSITIONS AND USE

[75] Inventors: Claus Schneider, Ingelheim am Rhein; Gerhard Walther, Bingen; Karl-Heinz Weber, Gau-Algesheim; Wolf D. Bechtel, Appenheim; Karin Böke-Kuhn, Gau-Algesheim, all of Fed. Rep. of Germany

[73] Assignee: Boehringer Ingelheim KG, Ingelheim am Rhein, Fed. Rep. of Germany

[21] Appl. No.: 630,376

[22] Filed: Jul. 23, 1984

Related U.S. Application Data

[62] Division of Ser. No. 466,100, Feb. 14, 1983, Pat. No. 4,482,559.

[30] Foreign Application Priority Data

Mar. 5, 1982 [DE] Fed. Rep. of Germany ....... 3207939

[51] Int. Cl.$^4$ ................. A61K 31/44; A61K 31/535; C07D 495/04
[52] U.S. Cl. .................... 514/212; 514/231; 514/301; 544/127; 546/114; 260/244.4
[58] Field of Search .............. 544/127; 546/114; 260/244.4; 514/212, 301, 231

[56] References Cited

U.S. PATENT DOCUMENTS 4,322,423  3/1982  Schneider .................... 546/114

Primary Examiner—Robert W. Ramsuer
Attorney, Agent, or Firm—Hammond & Littell, Weissenberger & Dippert

[57] ABSTRACT

Compounds of the formula

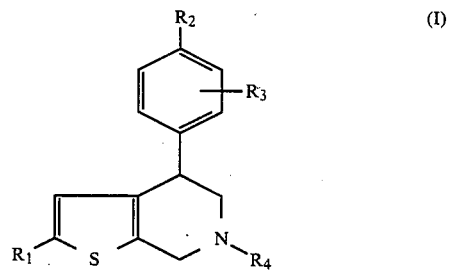

wherein $R_1$ is amino, acetylamino, hydroxymethyl, methoxymethyl or

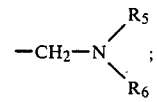

$R_2$ and $R_3$, which may be identical to or different from each other, are each hydrogen, fluorine, chlorine, bromine, trifluoromethyl, hydroxyl, methoxy, methyl or ethyl;

$R_4$ is straight or branched alkyl of 1 to 3 carbon atoms; and $R_5$ and $R_6$, which may be identical to or different from each other, are each hydrogen or alkyl of 1 to 4 carbon atoms or, together with each other and the nitrogen atom to which they are attached, form a 5-, 6- or 7-membered heterocyclic ring where, in the case of a 6-membered ring, a —CH$_2$-group in the ring may be replaced by an oxygen atom, and non-toxic, pharmacologically acceptable salts thereof. The compounds as well as their salts are useful as antidepressants.

7 Claims, No Drawings

4-PHENYL-4,5,6,7-TETRAHYDRO-THIENO[2,3-C]PYRIDINES AND SALTS THEREOF, COMPOSITIONS AND USE

This is a division of Ser. No. 466,100, filed Feb. 14, 1983 now U.S. Pat. No. 4,482,559.

This invention relates to novel basic-substituted 4-phenyl-4,5,6,7-tetrahydro-thieno[2,3-c]pyridines and non-toxic, pharmacologically acceptable acid addition salts thereof, to methods of preparing these compounds, to pharmaceutical compositions containing them as active ingredients, and to a method of using them as antidepressants.

More particularly, the present invention relates to a novel class of compounds represented by the formula

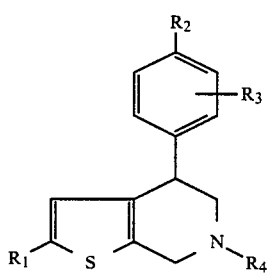

(I)

wherein $R_1$ is amino, acetylamino, hydroxymethyl, methoxymethyl or

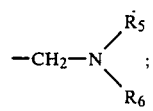

$R_2$ and $R_3$, which may be identical to or different from each other, are each hydrogen, fluorine, chlorine, bromine, trifluoromethyl, hydroxyl, methoxy, methyl or ethyl;

$R_4$ is straight or branched alkyl of 1 to 3 carbon atoms; and $R_5$ and $R_6$, which may be identical to or different from each other, are each hydrogen or alkyl of 1 to 4 carbon atoms or, together with each other and the nitrogen atom to which they are attached, form a 5-, 6- or 7-membered heterocyclic ring where, in the case of a 6-membered ring, a —CH$_2$— group in the ring may be replaced by an oxygen atom, and non-toxic, pharmacologically acceptable acid addition salts thereof.

A preferred subgenus thereunder is constituted by those compounds of the formula I wherein $R_1$ is hydroxymethyl or morpholinomethyl, and $R_2$, $R_3$ and $R_4$ have the meanings previously defined, and non-toxic, pharmacologically acceptable acid addition salts thereof.

The compounds embraced by formula I may be prepared by the following methods, starting from a 4-phenyl-thieno-[2,3-c]pyridine of the formula

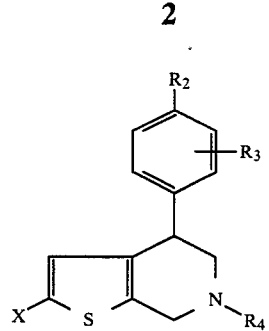

(II)

wherein $R_2$, $R_3$ and $R_4$ have the meanings previously defined, and

X is —NO$_2$, —CH$_2$Cl, —CH$_2$Br or

End products of the formula I wherein $R_1$ is amino are obtained by reducing the nitro group with a suitable reducing agent such as platinum-on-charcoal or palladium. The reduction is carried out in a solvent such as tetrahydrofuran, an alcohol, an ether or dioxane. Instead of using the above-mentioned reducing agents, it is also possible to dissolve the nitro compound in glacial acetic acid and reduce it with a solution of tin(II) chloride in hydrochloric acid to form the amino compound. The amino compound may then, if desired, be acetylated at the amino group in conventional manner, for instance by reacting it with acetic acid anhydride.

Compounds of the formula I wherein $R_1$ is

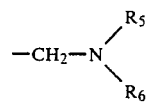

are obtained starting from a compound of the formula II wherein X is —CH$_2$Cl or —CH$_2$Br; this compound is reacted with the desired amine or with ammonia or with a compound which yields ammonia, either in an inert solvent such as an ether, dimethylformamide, tetrahydrofuran or an alcohol or with an excess of the amine which is used, preferably at temperatures between 50° and 100° C. The 2-methoxymethyl compound is also obtained via the corresponding 2-halomethyl starting compound of the formula II by reacting it with sodium methoxide in a lower alkanol, preferably methanol.

End products of the formula I wherein $R_1$ is alkylamino-methyl or hydroxy-methyl are preferably obtained by using the corresponding 2-formyl compounds of the formula II as starting compounds. In the former case, a formyl compound is reacted with an excess of a primary amine and with a reducing agent such as Raney nickel. The hydroxymethyl compound is obtained by the addition of sodium borohydride and a suitable solvent, such as dioxane.

It is also possible to obtain the 2-methoxymethyl compound from a corresponding 2-hydroxymethyl end product of the formula I by reacting the hydroxymethyl compound first with thionyl chloride and subsequently with sodium methoxide in methanol.

The following are examples of end products of the formula I which may be obtained by using the methods described above:

2-amino-4-(p-bromo-phenyl)-6-methyl-4,5,6,7-tetrahydro-thieno[2,3-c]pyridine, 2-amino-4-(p-chloro-phenyl)-6-methyl-4,5,6,7-tetrahydro-thieno[2,3-c]pyridine, 2-acetylamino-4-(p-bromo-phenyl)-6-methyl-4,5,6,7-tetrahydro-thieno[2,3-c]pyridine, 2-acetylamino-4-(p-chloro-phenyl)-6-methyl-4,5,6,7-tetrahydro-thieno[2,3-c]pyridine, 2-(amino-methyl)-4-(p-chloro-phenyl)-6-methyl-4,5,6,7-tetrahydro-thieno[2,3-c]pyridine, 2-(methylamino-methyl)-4-(p-methoxy-phenyl)-6-methyl-4,5,6,7-tetrahydro-thieno[2,3-c]pyridine, 2-(tert.butylamino-methyl)-4-(p-chloro-phenyl)-6-methyl-4,5,6,7-tetrahydro-thieno[2,3-c]pyridine, 2-(ethylamino-methyl)-4-(p-methoxy-phenyl)-6-methyl-4,5,6,7-tetrahydro-thieno[2,3-c]pyridine, 2-(diethylamino-methyl)-4-(p-bromo-phenyl)-6-methyl-4,5,6,7-tetrahydro-thieno[2,3-c]pyridine, 2-(diethylamino-methyl)-4-(p-chloro-phenyl)-6-methyl-4,5,6,7-tetrahydro-thieno[2,3-c]pyridine, 2-(morpholino-methyl)-4-(p-bromo-phenyl)-6-methyl-4,5,6,7-tetrahydro-thieno[2,3-c]pyridine, 2-(morpholino-methyl)-4-(p-chloro-phenyl)-6-methyl-4,5,6,7-tetrahydro-thieno[2,3-c]pyridine, 2-(morpholino-methyl)-4-(p-methoxy-phenyl)-6-methyl-4,5,6,7-tetrahydro-thieno[2,3-c]pyridine, 2-pyrrolidino-methyl)-4-(p-chloro-phenyl)-6-methyl-4,5,6,7-tetrahydro-thieno[2,3-c]pyridine, 2-(pyrrolidino-methyl)-4-(p-bromo-phenyl)-6-methyl-4,5,6,7-tetrahydro-thieno[2,3-c]pyridine, 2-(pyrrolidino-methyl)-4-(p-methoxy-phenyl)-6-methyl-4,5,6,7-tetrahydro-thieno[2,3-c]pyridine, 2-(hydroxy-methyl)-4-p-tolyl-6-methyl-4,5,6,7-tetrahydro-thieno[2,3-c]pyridine, 2-(hydroxy-methyl)-4-(p-methoxy-phenyl)-6-methyl-4,5,6,7-tetrahydro-thieno[2,3-c]pyridine, 2-(hydroxy-methyl)-4-(p-fluoro-phenyl)-6-methyl-4,5,6,7-tetrahydro-thieno[2,3-c]pyridine, 2-(methoxy-methyl)-4-(p-bromo-phenyl)-6-methyl-4,5,6,7-tetrahydro-thieno[2,3-c]pyridine, 2-(methoxy-methyl)-4-(p-chloro-phenyl)-6-methyl-4,5,6,7-tetrahydro-thieno[2,3-c]pyridine, 2-(hydroxy-methyl)-4-(3,4-dimethoxy-phenyl)-6-methyl-4,5,6,7-tetrahydro-thieno[2,3-c]pyridine, 2-(hydroxy-methyl)-4-(3,4-dihydroxy-phenyl)-6-methyl-4,5,6,7-tetrahydro-thieno[2,3-c]pyridine, and 2-(hexamethyleneimino-methyl)-4-(3,4-dichloro-phenyl)-6-methyl-4,5,6,7-tetrahydro-thieno[2,3-c]pyridine.

The starting compounds of the formula II may be obtained by known methods.

A nitro group may be introduced into the 2-position of the molecule by nitrating the compound which is unsubstituted at this point with trifluoroacetic acid and fuming nitric acid, while cooling.

Compounds wherein X is halomethyl may be obtained, for example, by reacting the corresponding 2-methyl comound with an N-halo-succinimide in the presence of a radical starter, such as azo-bis-isobutyronitrile, while refluxing.

2-Formyl starting compounds may be obtained by adding butyl lithium to the corresponding 2-halo compound in absolute ether at room temperature, and subsequently adding dimethylformamide, while cooling.

It is possible, but not absolutely essential to isolate the starting compounds of the formula II thus prepared; they may also be formed in situ for the reaction to prepare the desired end products.

The compounds of the formula I are basic and therefore form addition salts with inorganic or organic acids. Examples of non-toxic, pharmacologically acceptable acid addition salts are those formed with hydrohalic acid, sulfuric acid, phosphoric acid, an aminosulfonic acid, formic acid, acetic acid, propionic acid, lactic acid, glycolic acid, gluconic acid, maleic acid, succinic acid, tartaric acid, benzoic acid, salicylic acid, citric acid, ascorbic acid, p-toluenesulfonic acid, hydroxyethane sulfonic acid or the like.

The following examples illustrate the present invention and will enable others skilled in the art to understand it more completely. It should be understood, however, that the invention is not limited solely to the particular examples given below.

EXAMPLE 1

2-Acetylamino-4-(p-bromo-phenyl)-6-methyl-4,5,6,7-tetrahydro-thieno[2,3-c]pyridine 4 gm (0.01 mol) of 4-(p-bromo-phenyl)-6-methyl-2-nitro-4,5,6,7-tetrahydro-thieno[2,3-c]pyridine were suspended in 20 ml of glacial acetic acid, and the suspension was admixed with a solution of 20 gm of tin(II)-chloride in 40 ml of concentrated hydrochloric acid. After the reaction had gone to completion ice was added, and the solution was made alkaline and extracted with ether. After the solvent had been evaporated, the residue was combined with 25 ml of acetic acid anhydride, and the mixture was heated at 50° C. for a short time. Then, water was added, and the resulting mixture was made alkaline and extracted with ethyl acetate.

After the solvent had been removed by evaporation, the crystals obtained were suction-filtered off. Yield: 2 gm (55% of theory); m.p. 218°–220° C. (decomposition).

The starting compound was obtained by the following method:

25 ml of fuming nitric acid were added dropwise to 14.5 gm (0.047 mol) of 4-(p-bromo-phenyl)-6-methyl-4,5,6,7-tetrahydro-thieno[2,3-c]pyridine in 100 ml of trifluoroacetic acid, while cooling, so that the temperature did not exceed 20° C. After all the nitric acid had been added, the mixture was stirred for a further 30 minutes. The reaction mixture was then poured over ice, concentrated ammonia was added until the mixture reacted alkaline, and the mixture was then extracted with methylene chloride. After the solvent had been evaporated, the residual 4-(p-bromo-phenyl)-6-methyl-2-nitro-4,5,6,7-tetrahydro-thieno[2,3-c]pyridine was crystallized as its hydrochloride from alcoholic hydrochloric acid.

Yield: 12 gm (66% of theory); m.p. 205°–207° C. (decomposition).

EXAMPLE 2

2-Amino-4-p-chlorophenyl-6-methyl-4,5,6,7-tetrahydro-thieno-[2,3-c]pyridine 7 gm (0.0023 mol) of 4-p-chlorophenyl-6-methyl-2-nitro-4,5,6,7-tetrahydro-thieno[2,3-c]pyridine were reduced with 0.7 gm of platinum-on-charcoal in 70 ml of tetrahydrofuran/ethanol (1:1) for several hours under a hydrogen pressure of 5 bars. After the catalyst had been filtered off, the maleate of the title compound was obtained by the addition of ethanolic maleic acid.

Yield: 5.4 gm (60% of theory); m.p. 165°–166° C. (decomposition).

EXAMPLE 3

2-(Morpholino-methyl)-4-(p-bromo-phenyl)-6-methyl-4,5,6,7-tetrahydro-thieno[2,3-c]pyridine A mixture of 6.46 gm (0.02 mol) of 4-(p-bromo-phenyl)-2,6-dimethyl-4,5,6,7-tetrahydro-thieno[2,3-c]pyridine, 50 ml of carbon tetrachloride, 2.6 gm of N-bromo-succinimide and 0.1 gm of azo-bis-isobutyronitrile was heated at its boiling point for several hours. Then, the succinimide formed was suction-filtered off and the solvent was evaporated. Excess morpholine was slowly added to the residue, and the resulting mixture was stirred for 10 minutes at 50° C. The title compound was extracted from the aqueous phase with ether. It crystallized from acetone/maleic acid in the form of the dimaleate.

Yield: 5.85 gm (46% of theory);
m.p. 155°–156° C. (decomposition).

EXAMPLE 4

2-(Methoxy-methyl)-4-(p-chloro-phenyl)-6-methyl-4,5,6,7-tetrahydro-thieno[2,3-c]pyridine 2.79 gm (0.01-ol) of 4-(p-chloro-phenyl)-2,6-dimethyl-4,5,6,7-tetrahydro-thieno[2,3-c]pyridine were dissolved in 50 ml of carbon tetrachloride, the solution was heated at its boiling point with 1.8 gm of N-bromo-succinimide and 0.1 gm of azo-bis-isobutyronitrile for several hours. The resulting succinimide was suction-filtered off, and the solvent was removed in a rotary evaporator. The residue was admixed with a solution of 0.01 mol of sodium methoxide in methanol, and the mixture was heated at its boiling point for a short time. Then, water was added, and the resulting mixture was extracted with ether. Upon addition of etheral hydrochloric acid to the extract, the hydrochloride of the title compound crystallized out.

Yield: 1.74 gm (53% of theory);
m.p. 238°–239° C. (decomposition).

EXAMPLE 5

2-(Hydroxy-methyl)-6-methyl-4-p-tolyl-4,5,6,7-tetrahydro-thieno[2,3-c]pyridine 22 gm of 2-formyl-6-methyl-4-p-tolyl-4,5,6,7-tetrahydro-thieno[2,3-c]pyridine were dissolved in 100 ml of dioxane, and the solution was slowly admixed with 4 gm of sodium borohydride in 50 ml of water. After the reaction had ceased, excess sodium borohydride was destroyed with hydrochloric acid, and the reaction mixture was made alkaline with ammonia. The title compound was extracted from the alkaline solution with ether, and precipitated as the hydrochloride.

Yield: 12.3 gm (58% of theory);
m.p. 238°–239° C. (ethanol).

The starting compound was obtained as follows:

A solution of 0.15 mol of butyl lithium in n-hexane was added dropwise to a solution of 32.3 gm (0.1 mol) of 2-bromo-6-methyl-4-p-tolyl-4,5,6,7-tetrahydro-thieno[2,3-c]pyridine in 230 ml of absolute ether at −30° C., and the resulting mixture was stirred for 2 hours at room temperature. Then, 20 ml of dimethylformamide were added slowly at −30° C. After the reaction had ceased, first ice and then 2N hydrochloric acid were added. The mixture was neutralized with ammonia and extracted with ethyl acetate.

Yield of 2-formyl-6-methyl-4-tolyl-4,5,6,7-tetrahydro-thieno[2,3-c]pyridine: 22 gm (80% of theory); light yellow oil.

EXAMPLE 6

2-(Methylamino-methyl)-4-(p-methoxy-phenyl)-6-methyl-4,5,6,7-tetrahydro-thieno[2,3-c]pyridine A mixture of 2.87 gm (0.01 mol) of 2-formyl-4-(p-methoxy-phenyl)-6-methyl-4,5,6,7-tetrahydro-thieno[2,3-c]pyridine (prepared analogous to Example 5; light yellow oil), 70 ml of tetrahydrofuran, an excess of methylamine, and Raney nickel was kept at a temperature of 60° C. for several hours under a hydrogen pressure of 5 bar. After the catalyst had been removed by suction filtration, the title compound was precipitated in the form of the dimaleate by the addition of ethanolic maleic acid.

Yield: 3.4 gm (65% of theory);
m.p. 143°–144° C.

EXAMPLE 7

2-(Morpholino-methyl)-4-(p-chloro-phenyl)-6-methyl-4,5,6,7-tetrahydro-thieno[2,3-c]pyridine.

4.54 gm (0.02 mol) of 2-(hydroxy-methyl)-4-(p-chloro-phenyl)-6-methyl-4,5,6,7-tetrahydro-thieno[2,3-c]-pyridine were heated in 30 ml of ethylene chloride with an excess of thionyl chloride. After the reaction had ceased, the mixture was concentrated by evaporation in vacuo, an excess of morpholine was slowly added thereto, and the resulting mixture was stirred at 50° C. for 10 minutes. The title compound was extracted from the aqueous phase with ether. It was crystallized from acetone/maleic acid in the form of the dimaleate.

Yield: 6.2 gm (52% of theory);
m.p. 162°–163° C. (decomposition).

EXAMPLE 8

2-(Methoxy-methyl)-4-(p-chloro-phenyl)-6-methyl-4,5,6,7-tetrahydro-thieno[2,3-c]pyridine 4.54 gm (0.02 mol) of the 2-hydroxymethyl compound used as the starting material in Example 7 were treated with thienyl chloride as described in Example 7. After the reaction had ceased, 0.02 mol of sodium methoxide in methanol was added, and the resulting mixture was heated at its boiling points for a short time. Then, water was added, and the mixture was extracted with ether. The title compound was precipitated from the extract in the form of the hydrochloride.

Yield: 4.2 gm (64% of theory);
m.p. 238°–239° C. (decomposition).

The compounds of the formula I listed in the following table were also obtained by the methods described above:

| Example | $R_1$ | $R_2$ | $R_3$ | $R_4$ | M.p. | Salt |
|---|---|---|---|---|---|---|
| 9 | —NH$_2$ | Br | H | CH$_3$ | 145–147 (Decomp.) | Maleate |
| 10 | —NH—CO—CH$_3$ | Cl | H | CH$_3$ | 227–229 (Decomp.) | |

-continued

| Example | R₁ | R₂ | R₃ | R₄ | M.p. | Salt |
|---|---|---|---|---|---|---|
| 11 | $H_2N-CH_2$ | Cl | H | $CH_3$ | 186–187 (Decomp.) | Dimaleate |
| 12 | tert.butyl-NH—$CH_2$— | Cl | H | $CH_3$ | 215–216 (Decomp.) | " |
| 13 | $(C_2H_5)_2N-CH_2-$ | Br | H | $CH_3$ | 117–118 (Decomp.) | " |
| 14 | $(C_2H_5)_2N-CH_2-$ | Cl | H | $CH_3$ | 75 (Decomp.) | " |
| 15 | 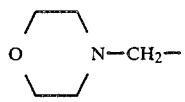 | $OCH_3$ | H | $CH_3$ | 156–157 (Decomp.) | " |
| 16 | 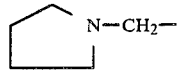 | Cl | H | $CH_3$ | 172–173 (Decomp.) | " |
| 17 | 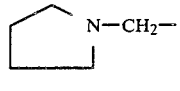 | Br | H | $CH_3$ | 169–170 (Decomp.) | " |
| 18 | 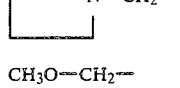 | $OCH_3$ | H | $CH_3$ | 178–179 (Decomp.) | " |
| 19 | $CH_3O-CH_2-$ | Br | H | $CH_3$ | 167–168 (Decomp.) | Methane-sulfonate |
| 20 | $HO-CH_2-$ | $OCH_3$ | H | $CH_3$ | 221–222 | Chloride |
| 21 | $C_2H_5-NHCH_2-$ | $OCH_3$ | H | $CH_3$ | 147–148 | Dimaleate |
| 22 | (azepan-N—CH₂) | Cl | m-Cl | $CH_3$ | 172–173 | Chloride |
| 23 | $HO-CH_2-$ | H | H | $CH_3$ | 220–221 | " |
| 24 | $HO-CH_2-$ | F | H | $CH_3$ | 210–211 | " |

The compounds of the present invention, that is, those embraced by formula I above and their non-toxic, pharmacologically acceptable salts, have useful pharmacodynamic properties. More particularly, they exhibit antidepressant activity in warm-blooded animals, such as mice, and especially produce a thymoleptic (mood elevating) effect and a central nervous system stimulating effect.

The test used for determining antidepressant properties was reserpine antagonism, namely the reversal of the hypothermic effect caused by reserpine. This test was carried out on mice, using five animals per dose. 17 hours after the intraperitoneal administration of 2 mg/kg of reserpine, the peripheral body temperature was measured at an ambient temperature of 19° C. Then, the test compound was administered by the oral route, and the body temperature was measured after 1, 3, 5 and 7 hours had elapsed. A median effective dose ($ED_{50}$) was determined for each period of measurement. This is the dose at which the body temperature of the animals treated with reserpine is brought closer to the normal temperature of the untreated control animals by 50%.

The following table shows the results of this test for a few representative species of the genus represented by formula I:

| Compound | Reserpine antagonism after mg/kg | | | | $LD_{50}$ in the mouse by oral route |
|---|---|---|---|---|---|
| | 1 | 3 | 5 | 7 hrs. | |
| 2-(Hydroxy-methyl)-6-methyl-4-p-tolyl-4,5,6,7-tetrahydro-thieno[2,3-c]pyridine hydrochloride | 2.5 | 0.24 | 2.5 | >10 | ~740 |
| 2-(Morpholino-methyl)-4-(p-bromo-phenyl)-6-methyl-4,5,6,7-tetra-hydro-thieno[2,3-c]pyridine dimaleate | 22 | 1.7 | 1.7 | 10.0 | >640 |
| 2-(Morpholino-methyl)-4-(p-chloro-phenyl)-6-methyl-4,5,6,7-tetrahydro-thieno-[2,3-c]pyridine dimaleate | >40 | 2.6 | 12.0 | 2.5 | >640 |

For pharmaceutical purposes the compounds of the present invention are administered to warm-blooded animals perorally, parenterally or rectally as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups, suppositories and the like. An effective amount of the compounds according to the present invention is from 0,0166 to 1,25 mgm/kg body weight, preferably 0,083 to 0,83 mgm/kg body weight.

The following examples illustrate a few pharmaceutical compositions comprising a compound of the present invention as an active ingredient and represent the best modes contemplated of using the invention. The parts are parts by weight unless otherwise specified.

EXAMPLE 25

Coated tablets

The tablet composition is compounded from the following ingredients:

| | |
|---|---|
| 2-(Hydroxy-methyl)-6-methyl 4-p-tolyl-4,5,6,7-tetrahydro-thieno[2,3-c]pyridine hydrochloride | 25.0 parts |
| Lactose | 50.0 parts |
| Corn starch | 22.0 parts |
| Gelatin | 2.0 parts |
| Magnesium stearate | 1.0 parts |
| Total: | 100.0 parts |

Preparation

A mixture of the active ingredient with the lactose and the corn starch is moistened with an aqueous 10% solution of the gelatin and granulated through a screen with a mesh size of 1 mm, then dried at 40° and again passed through a screen. The granules thus obtained are admixed with the magnesium stearate and compressed into 100 mg-tablets. The tablet cores thus obtained are coated in the usual way with a thin shell consisting essentially of a mixture of sugar, titanium dioxide, talcum and gum arabic. The finished coated tablets are polished with beeswax. Weight of finished coated tablet: 200 mg.

EXAMPLE 26

Tablets

The tablet composition is compounded from the following ingredients:

| | |
|---|---|
| 2-(Morpholino-methyl)-4-(p-bromo-phenyl)-6-methyl-4,5,6,7-tetra-hydro-thieno[2,3-c]pyridine dimaleate | 10.0 parts |
| Lactose | 40.0 parts |
| Corn starch | 44.0 parts |
| Magnesium stearate | 1.0 parts |
| Total | 100.0 parts |

Preparation

A mixture of the active ingredient and the magnesium stearate is granulated with an aqueous solution of the soluble starch, and the granules are dried and intimately mixed with the lactose and the corn starch. The mixture is then compressed into 100 mg-tablets each containing 10 mg of the active ingredient.

EXAMPLE 27

Suppositories

The suppository composition is compounded from the following ingredients:

| | |
|---|---|
| 2-(Morpholino-methyl)-4-(p-chloro-phenyl)-6-methyl-4,5,6,7-tetra-hydro-thieno[2,3-c]pyridine dimaleate | 10.0 parts |
| Suppository base (e.g. cocoa butter) | 1690.0 parts |
| Total | 1700.0 parts |

Preparation

The finely powdered active ingredient is stirred into the molten suppository base, which has been cooled to 40° C., using an immersion homogenizer. At 35° C., 1700 mg-portions of the mixture are poured into slightly chilled suppository molds and allowed to harden therein.

EXAMPLE 28

Hypodermic solution

The solution is compounded from the following ingredients:

| | |
|---|---|
| 2-(Morpholino-methyl)-4-(p-methoxy-phenyl)-6-methyl-4,5,6,7-tetra-hydro-thieno[2,3-c]pyridine hydrochloride | 5.0 parts |
| Sodium pyrosulfite | 1.0 parts |
| Disodium salt of EDTA | 0.5 parts |
| Sodium chloride | 8.5 parts |
| Double-distilled water q.s. ad | 1000.0 parts |

Preparation

The active ingredient and the excipients are dissolved in a sufficient amount of double-distilled water, and then the required quantity of double-distilled water is added to give the desired concentration. The solution is filtered and filled into 1 cc-ampules under aseptic conditions. Finally, the ampules are strilized and sealed. Each ampule contains 5.0 mg of the active ingredient.

Any one of the other compounds embraced by formula I or a non-toxic, pharmacologically acceptable salt thereof may be substituted for the particular active ingredient in Examples 25 through 28. Likewise, the amount of active ingredient in these illustrative examples may be varied to achieve the dosage unit range set forth above, and the amounts and nature of the inert pharmaceutical carrier ingredient may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

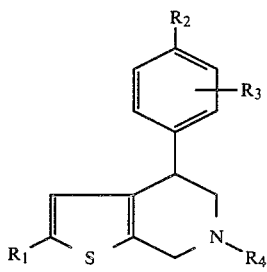

wherein

R₁ is amino,

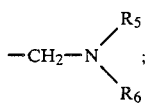

R₂ and R₃ are each hydrogen, fluorine, chlorine, bromine, trifluoromethyl, hydroxyl, methoxy, methyl or ethyl;

R₄ is straight or branched alkyl of 1 to 3 carbon atoms; and

R₅ and R₆ are each hydrogen or alkyl of 1 to 4 carbon atoms or, together with each other and the nitrogen atom to which they are attached, form a 5-, 6- or 7-membered heterocyclic ring, a —CH₂— group in the ring may be replaced by an oxygen atom, or a non-toxic, pharmacologically acceptable salt thereof.

2. A compound of claim 1,
wherein
R₁ is morpholinomethyl, and
R₂, R₃, R₄ have the meanings defined in claim 1,
or a non-toxic, pharmacologically acceptable salt thereof.

3. A compound of claim 2, which is 2-(morpholino-methyl)-4-(p-bromo-phenyl)-6-methyl-4,5,6,7-tetrahydro-thieno[2,3-c]pyridine or a non-toxic, pharmacologically acceptable acid addition salt thereof.

4. A compound of claim 2, which is 2-(morpholino-methyl)-4-(p-chloro-phenyl)-6-methyl-4,5,6,7-tetrahydro-thieno[2,3-c]pyridine or a non-toxic, pharmacologically acceptable acid addition salt thereof.

5. A compound of claim 2, which is 2-(morpholino-methyl)-4-(p-methoxy-phenyl)-6-methyl-4,5,6,7-tetrahydro-thieno[2,3-c]pyridine or a non-toxic, pharmacologically acceptable acid addition salt thereof.

6. An antidepressant pharmaceutical composition consisting essentially of an inert pharmaceutical carrier and an effective antidepressant amount of a compound of claim 1.

7. The method of preventing or relieving depression in a warm-blooded animal in need thereof, which comprises perorally, parenterally or rectally administering to said animal an effective antidepressant amount of a compound of claim 1.

* * * * *